United States Patent
Kantrowitz

(12) 
(10) Patent No.: US 7,468,050 B1
(45) Date of Patent: Dec. 23, 2008

(54) LONG TERM AMBULATORY INTRA-AORTIC BALLOON PUMP

(75) Inventor: Allen B. Kantrowitz, Miami Beach, FL (US)

(73) Assignee: L. Vad Technology, Inc., Detroit, MI (US)

(*) Notice: Subject to any disclaimer, the term of this patent is extended or adjusted under 35 U.S.C. 154(b) by 580 days.

(21) Appl. No.: 10/746,543

(22) Filed: Dec. 24, 2003

Related U.S. Application Data

(60) Provisional application No. 60/436,690, filed on Dec. 27, 2002.

(51) Int. Cl.
*A61M 29/00* (2006.01)
(52) U.S. Cl. .................................... 604/96.01
(58) Field of Classification Search .................. 604/18, 604/96.01–99.03; 600/16–18
See application file for complete search history.

(56) References Cited

U.S. PATENT DOCUMENTS

| | | | |
|---|---|---|---|
| 3,504,662 A * | 4/1970 | Jones ......................... | 600/18 |
| 3,553,736 A | 1/1971 | Kantrowitz et al. | |
| 3,585,983 A | 6/1971 | Kantrowitz et al. | |
| 3,692,018 A * | 9/1972 | Goetz et al. .................. | 600/18 |
| 3,720,199 A | 3/1973 | Rishton et al. | |
| 3,752,162 A | 8/1973 | Newash | |
| 3,815,577 A | 6/1974 | Bucalo | |
| 3,826,241 A | 7/1974 | Bucalo | |
| 3,877,496 A | 4/1975 | Sperberg | |
| 3,906,549 A | 9/1975 | Bucalo | |
| 4,004,298 A | 1/1977 | Freed | |
| 4,051,840 A | 10/1977 | Kantrowitz et al. | |
| 4,077,394 A | 3/1978 | McCurdy | |
| 4,092,742 A | 6/1978 | Kantrowitz et al. | |
| 4,092,983 A | 6/1978 | Slivenko | |

(Continued)

FOREIGN PATENT DOCUMENTS

DE 2220513 11/1973

(Continued)

OTHER PUBLICATIONS

Intraaortic Balloon Pumping in Congestive Heart Failure, © 1994, Springer—Verlag, New York, Inc., Adrian Kantrowitz, Raul R. Cardona, John Au, and Paul S. Freed.

(Continued)

*Primary Examiner*—George Manuel
(74) *Attorney, Agent, or Firm*—Young Basile

(57) ABSTRACT

A long term intra-aortic balloon pump (LTIABP) includes an enlarged pumping chamber on the order of 50 cc to 65 cc, inclusive. The pumping chamber is an intra luminal, large volume, long term balloon pump. The balloon pump can include tapered longitudinal ends and/or be segmented into a plurality of pumping chamber segments, each pumping chamber subsegment separated by a flexible power conduit link, where the diameter of the pumping chamber subsegments are independent of one another such as decreasing in size as the subsegments are further from the heart to accommodate the decreasing diameter of the aorta. The LTIABP can be used with any skin connector, or can be used with a percutaneous access device (PAD). The PAD can be sized and shaped to be surgically implanted in any desired location of the patient corresponding to the particular entry selected for implantation of a temporary IABP or LTIABP.

24 Claims, 5 Drawing Sheets

U.S. PATENT DOCUMENTS

| | | | |
|---|---|---|---|
| 4,164,221 | A | 8/1979 | Bentley et al. |
| 4,183,357 | A | 1/1980 | Bentley |
| 4,321,914 | A | 3/1982 | Begovac et al. |
| 4,338,937 | A | 7/1982 | Lerman |
| 4,393,873 | A | 7/1983 | Nawash |
| 4,458,678 | A | 7/1984 | Yannas et al. |
| 4,485,096 | A | 11/1984 | Bell |
| 4,527,549 | A | 7/1985 | Gabbay |
| 4,539,999 | A | 9/1985 | Mans |
| 4,579,120 | A | 4/1986 | MacGregor |
| 4,581,020 | A | 4/1986 | Mittleman |
| 4,605,007 | A | 8/1986 | Heraly |
| 4,609,551 | A | 9/1986 | Caplan et al. |
| 4,630,597 | A | 12/1986 | Kantrowitz et al. |
| 4,634,422 | A | 1/1987 | Kantrowitz et al. |
| 4,645,504 | A | 2/1987 | Byers |
| 4,668,222 | A | 5/1987 | Poirier |
| 4,692,148 | A | 9/1987 | Kantrowitz et al. |
| 4,712,563 | A | 12/1987 | Link |
| 4,733,652 | A | 3/1988 | Kantrowitz et al. |
| 4,741,328 | A | 5/1988 | Gabbay |
| 4,774,960 | A | 10/1988 | Arnold et al. |
| 4,781,715 | A | 11/1988 | Wurzel |
| 4,782,817 | A | 11/1988 | Singh et al. |
| 4,785,795 | A | 11/1988 | Singh |
| 4,790,826 | A | 12/1988 | Elftman |
| 4,804,369 | A | 2/1989 | Lapeyre et al. |
| 4,809,681 | A | 3/1989 | Kantrowitz et al. |
| 4,810,246 | A | 3/1989 | Frisch et al. |
| 4,877,035 | A | 10/1989 | Bogen et al. |
| 4,888,011 | A | 12/1989 | Kung et al. |
| 4,897,081 | A | 1/1990 | Poirier et al. |
| 4,902,272 | A | 2/1990 | Milder et al. |
| 4,913,700 | A | 4/1990 | Kantrowitz et al. |
| 4,944,722 | A | 7/1990 | Carriker et al. |
| 4,955,861 | A | 9/1990 | Enegren et al. |
| 4,974,774 | A | 12/1990 | Nakagawa et al. |
| 5,045,051 | A | 9/1991 | Milder et al. |
| 5,048,532 | A | 9/1991 | Hickey |
| 5,089,016 | A | 2/1992 | Millner et al. |
| 5,098,397 | A | 3/1992 | Svensson et al. |
| 5,135,488 | A | 8/1992 | Foote et al. |
| 5,139,508 | A | 8/1992 | Kantrowitz et al. |
| 5,147,388 | A | 9/1992 | Yamazaki |
| 5,158,529 | A | 10/1992 | Kanai |
| 5,169,379 | A | 12/1992 | Freed et al. |
| 5,201,755 | A | 4/1993 | Klement |
| 5,219,326 | A | 6/1993 | Hattler |
| 5,234,457 | A | 8/1993 | Andersen |
| 5,242,374 | A | 9/1993 | Isoyama |
| 5,242,415 | A | 9/1993 | Kantrowitz et al. |
| 5,261,878 | A | 11/1993 | Galindo |
| 5,308,319 | A * | 5/1994 | Ide et al. .................. 600/18 |
| 5,312,364 | A | 5/1994 | Jacobs |
| 5,336,167 | A | 8/1994 | Sullivan et al. |
| 5,352,180 | A | 10/1994 | Candelon et al. |
| 5,356,378 | A | 10/1994 | Doan |
| 5,372,709 | A | 12/1994 | Hood |
| 5,387,192 | A | 2/1995 | Glantz et al. |
| 5,411,027 | A | 5/1995 | Wiklund et al. |
| 5,423,746 | A | 6/1995 | Burkett et al. |
| 5,445,622 | A | 8/1995 | Brown |
| 5,482,446 | A | 1/1996 | Williamson et al. |
| 5,514,079 | A | 5/1996 | Dillon |
| 5,637,088 | A | 6/1997 | Wenner et al. |
| 5,713,954 | A | 2/1998 | Rosenberg et al. |
| 5,735,897 | A | 4/1998 | Buirge |
| 5,746,709 | A | 5/1998 | Rom et al. |
| 5,810,708 | A | 9/1998 | Woodard et al. |
| 5,810,836 | A | 9/1998 | Hussein et al. |
| 5,827,171 | A | 10/1998 | Dobak et al. |
| 5,833,619 | A | 11/1998 | Freed et al. |
| 5,833,655 | A | 11/1998 | Freed et al. |
| 5,882,329 | A | 3/1999 | Patterson et al. |
| 5,904,666 | A | 5/1999 | DeDecker et al. |
| 5,906,579 | A | 5/1999 | Salm et al. |
| 5,910,103 | A * | 6/1999 | Saper et al. .................. 600/18 |
| 5,928,132 | A | 7/1999 | Leschinsky ................ 600/6.16 |
| 6,042,532 | A | 3/2000 | Freed et al. |
| 6,132,363 | A | 10/2000 | Freed et al. |
| 6,136,025 | A | 10/2000 | Barbut et al. ................. 623/3.1 |
| 6,210,318 | B1 | 4/2001 | Lederman .................... 600/18 |
| 6,395,026 | B1 | 5/2002 | Aboul-Hosn et al. ....... 623/3.13 |
| 6,468,200 | B1 * | 10/2002 | Fischi ......................... 600/18 |
| 6,511,412 | B1 | 1/2003 | Freed et al. |
| 6,532,964 | B2 | 3/2003 | Aboul-Hosn et al. ........ 128/898 |
| 6,749,598 | B1 | 6/2004 | Keren et al. ................. 604/508 |
| 7,374,531 | B1 * | 5/2008 | Kantrowitz ................. 600/18 |
| 2003/0105383 | A1 | 6/2003 | Barbut et al. .................. 600/16 |
| 2003/0130610 | A1 | 7/2003 | Mager et al. ............... 604/6.16 |

FOREIGN PATENT DOCUMENTS

| | | |
|---|---|---|
| EP | 0402872 | 12/1990 |
| EP | 0684022 A2 | 10/1995 |
| WO | WO 95/10989 | 4/1995 |
| WO | WO 2004/054641 | 7/2004 |
| WO | WO 01/83016 | 11/2004 |

OTHER PUBLICATIONS

American Journal of Cardiology, © 1988, Intraaortic Balloon Pumping for Prolonged Circulatory Support, Paul S. Freed, MS, Tarik Wasfie, MD, Barina Zado, MD, and Adrian Kantrowitz, MD.

Surgery © 1969, A Dynamic Aortic Patch as a Permanent Mechanical Auxiliary Ventricle: Experimental Studies, Eduard Sujansky, M.D., Steinar Tjonneland, M.D., Paul S. Freed, M.S., Adrian Kantrowitz, M.D.

Transplantation Proceedings © 1971, Current Status of Intraaortic Balloon Pump and Initial Clinical Experience with Aortic Patch Mechanical Auxiliary Ventricle, Adrian Kantrowitz, Joseph S. Krakauer, George Zorzi, Melvyn Rubenfire, Paul S. Freed, Steven Phillips, Marc Lipsius, Claudio Titone, Philip Cascade, and Dov Jaron.

Journal of Biomedical Materials Research, © 1978, Biocompatibility Tests of Components of an Implantable Cardiac Assist Device, Andreas F. Von Recum, Hiroji Imamura, Paul S. Freed, Adrian Kantrowitz, Shan-Te Chen, Merlin E. Ekstrom, Charles A. Baechler and Marion I. Bamhart.

Trans. Amer. Soc. Artif. Int. Organs © 1972, Initial Clinical Experience with a New Permanent Mechanical Auxiliary Ventricle: The Dynamic Aortic Patch, Adrian Kantrowitz, J. Krakauer, M. Rubenfire, D. Jaron, P.S. Freed, W. Welkowitz, P. Cascade, W.J. Wajszczuk, M. Lipsius, M. Ciborski, S. J. Phillips, and M.T. Hayden.

American Journal of Nursing, © 1973, Care of a Man with a Partial Artificial Heart, Roberta Nelson, Judy Smith, Ruth Drummond, Hilde Pollard, Joyce Billingsley, Miriam Nikkila.

Moore et al, "Microporcessor Based Controller for In-Series Cardiac Assistance," *Medical & Biological Engineering & Computing*, vol. 20, pp. 523-526 (Jul. 1982).

\* cited by examiner

LONG TERM AMBULATORY INTRA-AORTIC BALLOON PUMP

CROSS-REFERENCE TO RELATED APPLICATIONS

This application is a continuation of U.S. provisional patent application Ser. No. 60/436,690 filed Dec. 27, 2002, which is incorporated by reference herein in its entirety.

FIELD OF THE INVENTION

The present invention relates to an intra-aortic balloon pump insertable through a vessel entry of the patient, and more particularly to an intra-aortic balloon pump for long term ambulatory use powered through a percutaneous access device.

BACKGROUND OF THE INVENTION

Temporary intra-aortic balloon pumps are generally known for insertion through the femoral artery of the leg for emergency patient treatment. Temporary use of the pump was originally intended to last for only a few hours up to a few days for non-ambulatory patients in emergency situations. The temporary intra-aortic balloon pump is limited in size to prevent fully occluding the lumen of the aorta and/or any branch arteries, so that pressures within each location are free to equalize at all times, and in order to pass percutaneously via an introduction sheath through the smaller diameter of the femoral artery during insertion. Non-ambulatory patients restricted to bed can subsist with the level of cardiac assistance available from the relatively small (e.g. typically 30 to 40 cubic centimeters (cc)) volume of the temporary intra-aortic balloon pump. However, this relatively limited level of cardiac assistance is insufficient, and the typical location of insertion is undesirable, for ambulatory patients. In addition, the temporary intra-aortic balloon pump is typically tightly furled and wrapped in order to allow for insertion through a narrow introduction sheath. The furling and wrapping of the material raises concerns regarding damage to the material of the balloon pump which might possibly lead to premature failure when subjected to numerous pumping cycles, if prolonged use over a period greater than a few days is mandated for a particular patient. Further, the power supply conduit to the pump is of limited cross sectional area because of the use of a helium pumping medium in order to provide the desired level of responsiveness to correctly time the inflation and deflation of the temporary intra-aortic balloon pump with respect to the heart beat of the patient. The use of a helium pumping medium may not be as practical as the use of an air pumping medium in order to provide a simple cardiac assistance device for ambulatory patients.

In the original description of clinical use of the temporary IABP, the procedure described the open exposure of the femoral artery with end-to-side anastomosis of a short vascular graft. The graft was used as the vascular entry point. As the use of the temporary IABP grew internationally, many variants of this original concept were introduced to solve specific clinical dilemmas. These variants were introduced to permit use of the temporary IABP in patients with unusually small or stenotic femoral vessels, or in patients whose aorta was easily available during thoracotomy or in patients needing the temporary IABP as a bridge-to-transplant. Distal ischemic complications are a concern in many of these methods. Techniques that use an end-to-side vascular graft may be less prone to this complication. Variant vascular entry points that have been described for the temporary IABP have included: (1) open approach to the femoral artery with cannulation via an end-to-side vascular grafts; (2) percutaneous approach to the femoral artery; (3) open approach to the iliac artery; (4) retro peritoneal approach; (5) during open thoracotomy for a standard open-heart procedures, the open trans thoracic approach with direct cannulation with the aorta; (6) during open thoracotomy for standard open-heart procedures, the open trans thoracic approach with cannulation via end-to-side vascular graft; (7) large aortic caliber side graft for cul-de-sac placement; and (8) axillary artery approach with cannulation either directly or via an end-to-side vascular graft.

To alleviate some of the limitations and difficulties associated with the catheter-based temporary intra-aortic balloon pump, a permanent balloon pump in the form of an elliptical patch supporting the pumping chamber was disclosed in U.S. Pat. No. 4,630,597 for incorporation into the wall of the aorta by a surgeon. Permanent use of the pump was intended to last for a prolonged period of time extending from a few months up to several years for ambulatory patients who required more than just temporary cardiac assistance. The procedure required the surgeon to perform a left thoracotomy, cross clamp the aorta, and then fashion a suture line around the perimeter of the patch. An advantage of this configuration was that the geometry of the thoracic aorta is expanded, allowing the displacement volume of the pumping chamber to be in the desired range of 60 cubic centimeters (cc) to 65 cubic centimeters (cc), inclusive, thereby enhancing the clinical effectiveness of the CARDIOVAD® device.

U.S. Pat. No. 5,484,385 discloses an intra-aortic balloon catheter. This patent addresses the potential problem of a thin wall balloon failing by rupture believed to be due to abrasion between the thin wall of the balloon and the inner wall surface of the aorta. Typically, a balloon catheter has a thin wall thickness in order to provide for furling the balloon into a small uniform diameter dimension for surgical insertion through the femoral artery to a position below the aortic arch and the left subclavian artery before unfurling. The patent proposes increased wall thickness and reduced outer diameter of the balloon to provide a narrower tapered distal end of the balloon within the narrower portion of the aorta with the narrower portion of the aorta. However, this patent does not recognize or address the potential tortuosity of the aorta that typically can occur in patients, where the aorta is not smooth and uniform in a two-dimensional plane as depicted in medical books, but rather twists and turns through three-dimensional space within the body cavity creating greater difficulty in properly positioning and operating a balloon pump within the descending aorta of the patient.

U.S. Pat. No. 4,527,549 discloses a method of an means for intra-aortic assist. The patent asserts that the position of the balloon is more important than the size of the balloon, and that the proper position for a balloon is at the root of the aorta right above the valve in the ascending portion of the aorta. In order to traverse the aortic arch, the patent proposes preforming the device to follow the aortic arch. While the patent suggests the use of multi-segment balloons, it specifically teaches that the appropriate position for the first balloon is immediately above the valve in the ascending portion of the aorta. This patent does not recognize the difficulty in positioning a balloon within the ascending portion of the aorta and/or the difficulty in passing a preformed portion corresponding to the arch of the ascending aorta through the serpentine tortuous descending portion of the aorta. The patent does not address the potential clinical danger of stroke created by a catheter moving across the entrances to the arch vessels (e.g. the left subclavian artery, the left common carotid artery, and the innominate artery). The clinical danger of stroke, by way of example and not limitation, can be linked to: (1) risk of dislodgment of embolus or plaque into the arch vessels during insertion of the balloon pump around the arch into the ascending aorta; (2) risk of occlusion of the arch vessels; (3) risk of repeated abrading action against the surface of the arch and entrance to the arch vessels; and (4) risk of dislodgment of embolus or plaque during withdrawal or replacement of the balloon pump. In summary, the patent does not recognize that the risks associated with positioning the proximal balloon in the ascending aorta outweigh the benefits achieved, and that a larger size balloon in the descending aorta alleviates the need to entertain the risk of entering the ascending balloon in order to provide the amount of assistance desired for an ambulatory patient.

U.S. Pat. No. 6,468,200, U.S. Pat. No. 3,791,374, and U.S. Pat. No. 3,504,662 each disclose segmented balloon pumps adapted to be actuated at different rates. For example, U.S. Pat. No. 3,504,662 discloses actuation of the middle compartment prior to or at a more rapid rate than the end compartments. U.S. Pat. No. 6,468,200 discloses the chambers are inflated sequentially beginning with the chamber closest to the aortic root, in order to advance the blood in the downstream direction. Each of these patents teaches the desirability of a temporal sequence of inflation and/or deflation, even though such procedures are of undetermined effectiveness and accordingly are not well established as providing the amount of assistance desired for an ambulatory patient.

An article published by The Society of Thoracic Surgeons in 2002 entitled "Ambulatory Intraaortic Balloon Pump Use as Bridge to Heart Transplant" taught the advantage of using an catheter based intraaortic balloon pump positioned in the descending aorta accessed through an expanded polytetrafluoroethylene vascular conduit graft to the left axillary artery. The procedure allowed the patient to be ambulatory, and allowed multiple exchanges of the catheter based intraaortic balloon pump for extended use (12 days to 70 days). The positioning of the intraaortic balloon was similar to the conventional position, except the distal end of the balloon was maintained above the renal arteries and the proximal end of the balloon was positioned just below the subclavian artery in the descending aorta. While pointing out the benefits of maintaining ambulatory patients, the article did not reflect the desirability of increased balloon pump volume for ambulatory patients, and/or the desirability of increased conduit diameter for maintaining balloon pump cycle timing for larger volume balloon pumps, and/or the desirability of a percutaneous access device for connecting the catheter based intraaortic balloon pump to the drive system for an ambulatory patient.

SUMMARY OF THE INVENTION

The CARDIOVAD® device was optimized for permanent (i.e. months up to years) implantation, while the catheter-based temporary intra-aortic balloon pump was optimized for simple insertion in anticipation of short term use (i.e. hours up to days). The present invention is a variant of the CARDIOVAD® permanent balloon pump device, and the temporary intra-aortic balloon pump to retain the advantages of both systems, while eliminating some of the disadvantages. The present invention, referred to herein as a long term intra-aortic balloon pump (LTIABP), is intended for prolonged use (i.e. weeks up to years) for ambulatory patients, and retains the advantages of permanent implantation while simplifying the surgical implantation technique in a fashion reminiscent of the temporary intra-aortic balloon pump (IABP). The present invention modifies the structural configuration of the temporary intra-aortic balloon pump in order to allow use as a long term intra-aortic balloon pump. The first modification according to the present invention is to increase the stroke volume for more clinical effectiveness in ambulatory patients by providing a large volume (i.e. 50 cubic centimeters (cc) to 65 cubic centimeters (cc), inclusive) displacement blood pump, and by providing an increased cross sectional area for the power conduit to permit the use of alternative pumping mediums, preferably compressed air or any other gas, such as helium. A second modification according to the present invention is at the skin entrance of the power/signal conduit.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1C:
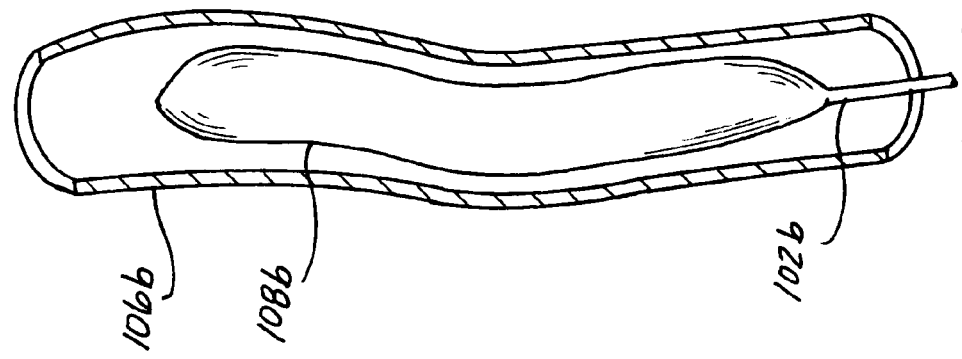
FIG. 1C is a detailed cross-sectional view of the single chamber balloon pump of FIG. 1A in an inflated state after insertion through a lower body skin entry point and/or lower body vascular entry point.

Various embodiments are shown throughout the Figures illustrating the present invention, and include common elements in different structural configurations where common elements are designated with a common base numeral and differentiated with a different alphabetic designation for the various embodiments. Descriptions for the base numeral designations are considered to be generic to the different alphabetic extensions added to the alternative embodiments except as specifically noted herein.

The present invention provides a pumping chamber lying completely within the lumen of the aorta rather than being embedded or implanted in the wall of the aorta. By way of example and not limitation, a surgeon can anastomose a length of vascular graft end-to-end directly to the aorta and use this graft as the aortic cannulation point. The vascular graft can be long enough to reach the subcutaneous skin layer, thereby simplifying exchange of the LTIABP if exchange becomes necessary due to clinical circumstances. It is expected that the placement of the graft and the LTIABP could be performed either with open surgical techniques, percutaneous techniques, or with endoscopic techniques via the thoracic cavity, the retroperitoneal space or the thoracic outlet or other anatomic sites.

According to the present invention, the size of the blood pump 108 and the power/signal conduit 102 can both be made larger than in the case of the temporary IABP. This enlarged configuration allows for various advantages over the temporary IABP. A larger displacement volume for the LTIABP according to the present invention is desired for ambulatory patients compared with the temporary IABP, since ambulatory patients have larger circulatory demand requirements than sedentary patients. The long term ambulatory status of the patient would be best served by the use of air rather than helium as the pneumatic driving medium, thereby obviating the need for storage and periodic replacement of lost helium in the apparatus. Viscosity differences between air and helium necessitate the use of a larger diameter pneumatic power conduit 102 when air is used in order to preserve the dynamic responsiveness of the cardiac assist device.

First, to provide a larger displacement volume for the LTIABP, the pumping chamber 108a of the LTIABP according to the present invention is longer than that of the temporary IABP giving the LTIABP a larger stroke volume (improving its clinical effectiveness) compared with the temporary IABP. The longer length requires additional modifications, such as a tapered shape in order to minimize risk of injury to the subclavian, carotid, celiac, mesenteric and renal arteries. The longer length raises two concerns: intermittent occlusion of the entrance to major branch arteries and abrasion against the inner wall of the aorta in case of tortuous aorta. A tortuous aorta is a common presentation in many patients with cardiovascular disease sufficiently advanced to warrant consideration of mechanical support of the failing heart. These concerns are met with the design of the LTIABP according to the present invention by tapering the ends of the pumping chamber 108a and/or segmenting the pumping chamber into one or more subsegments 108, 110, 112, 114 each separated by a flexible power conduit 102 link. These links would allow the long axis of each segment of the pumping chamber to align with a local longitudinal axis of a local segment of the surrounding aortic lumen containing the corresponding inflatable chamber. Moreover, the diameter of each segment can be different. Thus, the segmented pumping chamber of the LTIABP according to the present invention, together with the intervening links, can allow the device according to the present invention to accommodate variations in the tortuous or serpentine shape of the aorta. This type of segmentation of the pumping chamber is distinguishable from mono-chamber temporary IABP devices which can not adapt to a tortuous aorta, and is distinguishable from multi-chamber temporary IABP devices which have been introduced in the past in order to influence the inflation and deflation characteristics, as well as timing and directionality characteristics, of the pumping chambers.

Second, the wall structure of the LTIABP according to the present invention can be more rugged when compared to the conventional temporary IABP, thereby improving the flex life. This permits selection of alternative materials and/or additional thickness of conventional materials, or layering wall structures to improve the flex life of the LTIABP device according to the present invention. The present invention does not require the tight furling necessary for conventional insertion of a temporary IABP device through the femoral artery. It is believed that tight furling may on occasion cause injury to the molecular structure of the conventional temporary IABP pumping membrane.

Third, according to the present invention, the power/signal conduit 102 can be of larger diameter thereby improving the performance characteristics of the system determined by that parameter; improving clinical effectiveness at high heart rates; and improving effectiveness with air (rather than helium) as the driving fluid. Allowing air as the driving fluid, in addition to helium, is an important advantage in long term use, since helium needs to be slowly replenished on an ongoing basis. However, in order to maintain the flow rate of air during use as the driving fluid, a large diameter pneumatic power conduit 102 is required.

The temporary IABP was originally intended as a device for short term (i.e. hours up to days) management of acute heart failure (CHF). Accordingly, the skin entry point was managed clinically as a simple catheter puncture site. After approximately 5-7 days, such skin puncture sites allow colonization of the catheter surface. Straight forward efforts to confine such bacterial colonization of catheter entry sites to the subcutaneous plane with a cuff (such as with the HICKMAN® and GROSHONG® catheters) can extend the useful lifetime of the catheter for weeks and months, but are not robust enough to reliably solve the bacterial contamination problem for months and years. The problem of long term percutaneous access for power and signal conduits was addressed in the percutaneous access device 10 (PAD) designed for use with the CARDIOVAD® permanent blood pump as disclosed in U.S. Pat. No. 5,833,655 which is incorporated by reference herein. An alternate percutaneous device is disclosed in U.S. Pat. No. 5,242,415 which is incorporated by reference herein. Preferably, the percutaneous access device in cultured with cells prior to the implantation by any suitable method, by way of example and not limitation, such as the methods described in U.S. Pat. No. 4,913,700 and U.S. Pat. No. 4,810,246 which are incorporated by reference herein. The percutaneous access device 10 can be adapted to convey the power/signal conduit 102 of the LTIABP according to the present invention. The PAD 10 provides for a stable interface to be established between the skin and the LTIABP device and also provides for a break away point in the conduit to allow the patient to be disconnected from the drive system P as clinical status permits.

As in the existing CARDIOVAD® permanent blood pump device, the present invention can include signal sensors implanted in locations separate from the pumping chamber or integrated into the pumping chamber and yet still be integrated into the percutaneous access device 10 (PAD) in order for the signal sensor leads to be passed through the skin to the LTIABP.

In summary, the LTIABP according to the present invention merges the simplified surgical implantation procedure of the catheter-based conventional temporary IABP with the advantages of the CARDIOVAD® permanent blood pump. The long term intra-aortic balloon pump according to the present invention uses an enlarged balloon pump with less severe folding and wrapping when compared with the conventional temporary IABP. If desired, ECG electrodes can be integrated into the balloon pump as is conventional, and can include at least one electrode, and preferably two or more electrodes. The power conduit delivering compressed fluid to the balloon pump can include an additional channel, possibly centrally located, allowing access for a guide wire, or placement of a pressure sensor, or for blood sample monitoring. The pressure sensor can take any suitable form from commercially available products, such as a conventional electrical strain gauge transducer or an optical based pressure transducer. If an alternative or supplement to a conventional pressure sensor is desired, the present invention can be used with a partial inflation and/or deflation cycle for blood pressure measurement as described in more detail in U.S. Pat. No. 5,833,619, U.S. Pat. No. 5,904,666, U.S. Pat. No. 6,042,532, U.S. Pat. No. 6,132,363, and/or U.S. Pat. No. 6,511,412, all of which are incorporated by reference herein in their entireties.

Figure 1B:
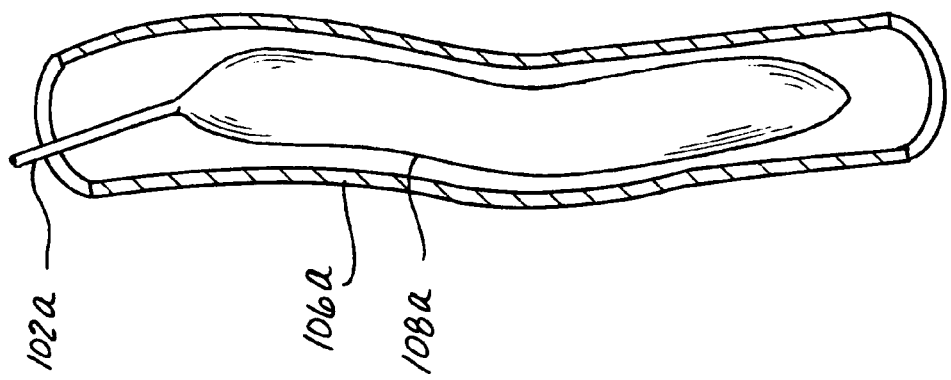
FIG. 1B is a detailed cross-sectional view of the single chamber balloon pump of FIG. 1A in an inflated state.
Figure 1A:
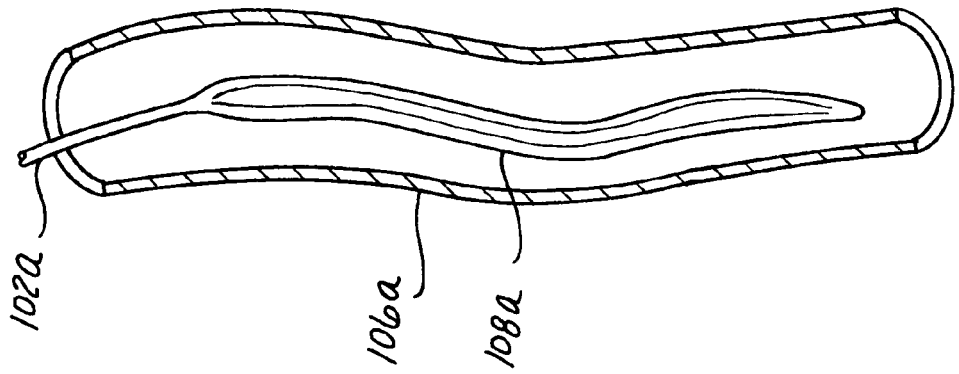
FIG. 1A is a detailed cross-sectional view of a vascular entry into the aorta illustrating a single chamber, large volume, long term intra-aortic balloon pump according to the present invention in a deflated state after insertion through an upper body skin entry point and/or upper body vascular entry point.
Figure 2C:
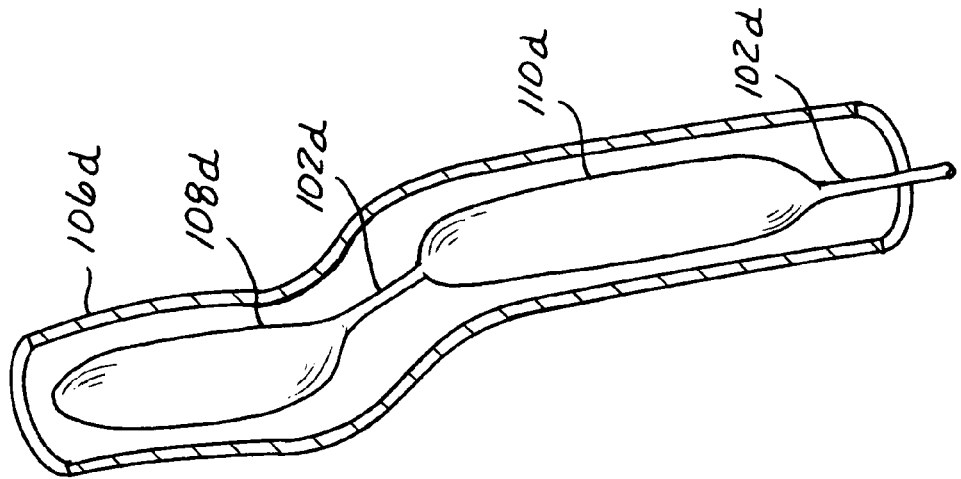
FIG. 2C is a detailed cross-sectional view of the double chamber balloon pump of FIG. 2A in an inflated state after insertion through a lower body skin entry point and/or lower body vascular entry point.
Figure 2B:
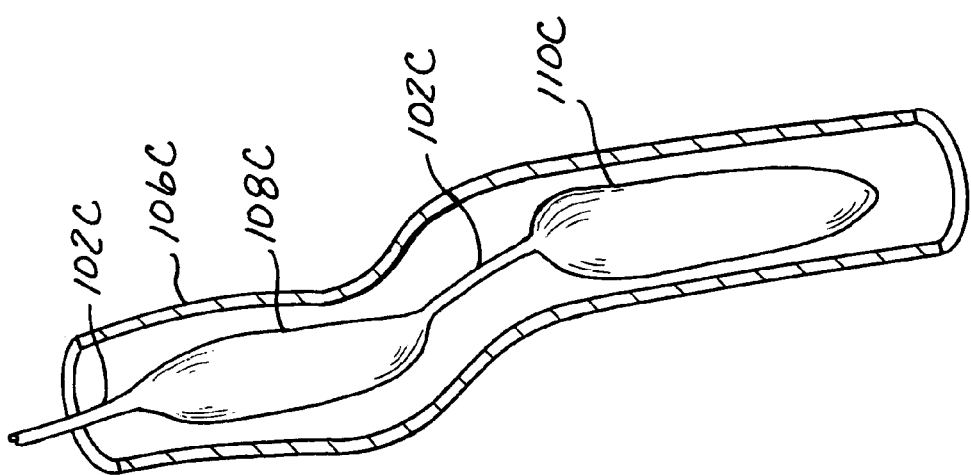
FIG. 2B is a detailed cross-sectional view of the double chamber balloon pump of FIG. 2A in an inflated state.
Figure 2A:
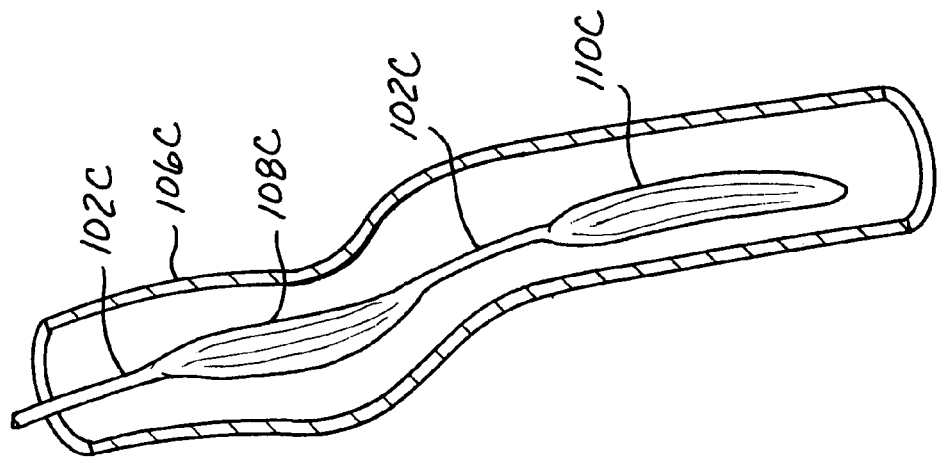
FIG. 2A is a detailed cross-sectional view of a vascular entry into the aorta illustrating a double chamber, large volume, long term intra-aortic balloon pump according to the present invention in a deflated state after insertion through an upper body skin entry point and/or upper body vascular entry point.
Figure 3C:
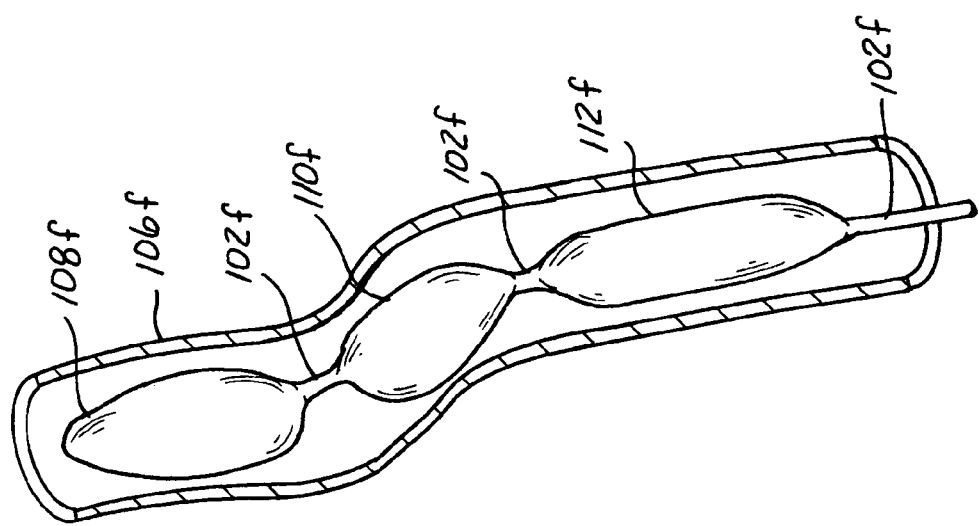
FIG. 3C is a detailed cross-sectional view of the triple chamber balloon pump of FIG. 2A in an inflated state after insertion through a lower body skin entry point and/or lower body vascular entry point.
Figure 3B:
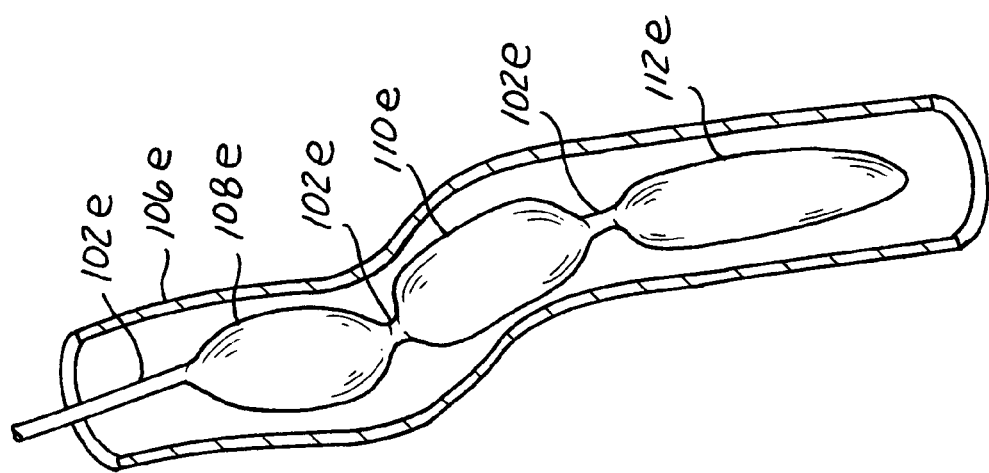
FIG. 3B is a detailed cross-sectional view of the triple chamber balloon pump of FIG. 2A in an inflated state.
Figure 3A:
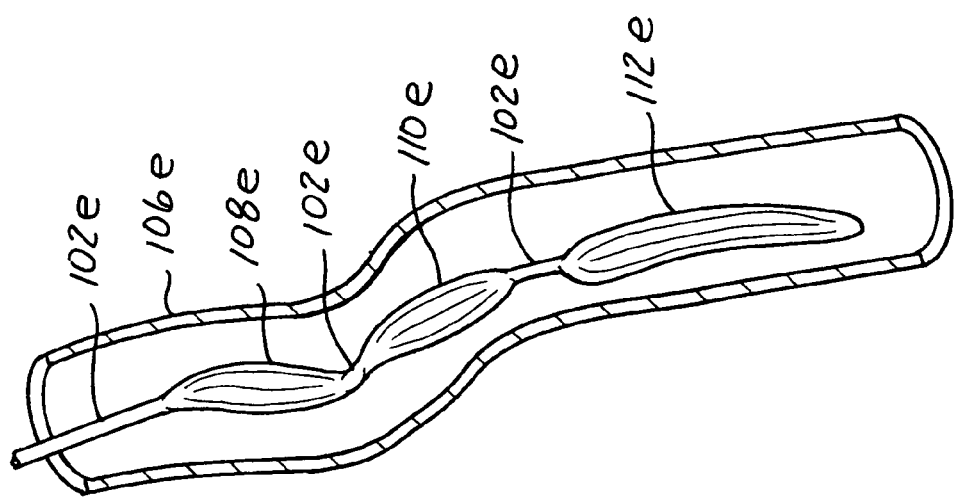
FIG. 3A is a detailed cross-sectional of a vascular entry into the aorta illustrating a triple chamber, large volume, long term intra-aortic balloon pump according to the present invention in a deflated state after insertion through an upper body skin entry point and/or upper body vascular entry point.
Figure 4C:
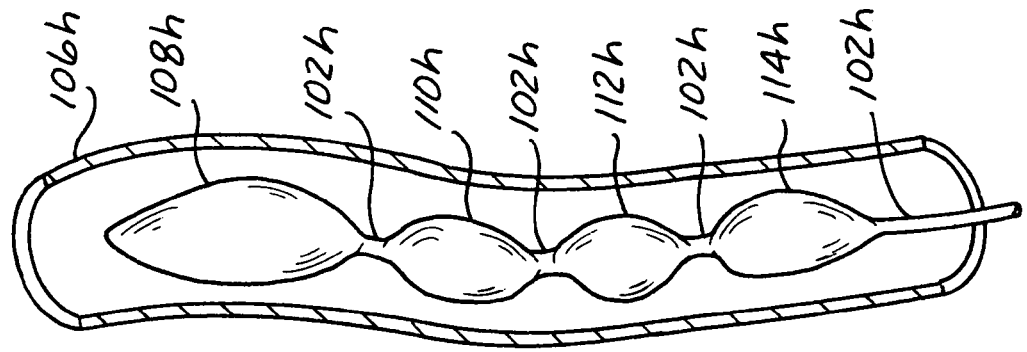
FIG. 4C is a detailed cross-sectional view of the quadruple chamber balloon pump of FIG. 2A in an inflated state after insertion through a lower body skin entry point and/or lower body vascular entry point.
Figure 4B:
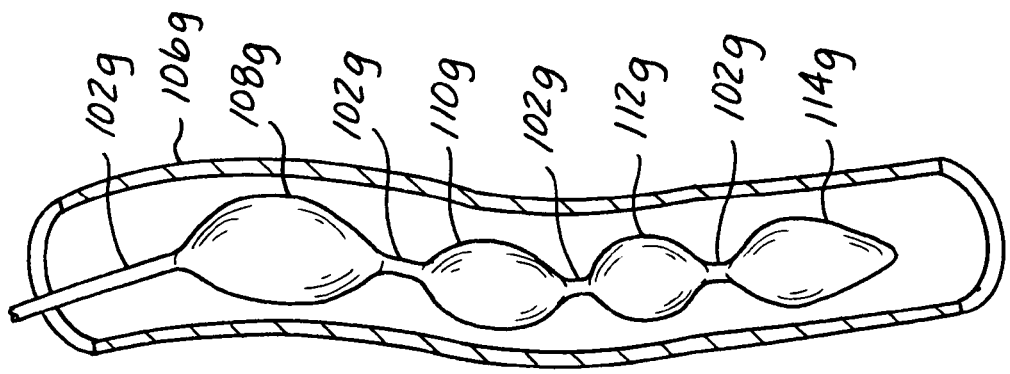
FIG. 4B is a detailed cross-sectional view of the quadruple chamber balloon pump of FIG. 2A in an inflated state.
Figure 4A:
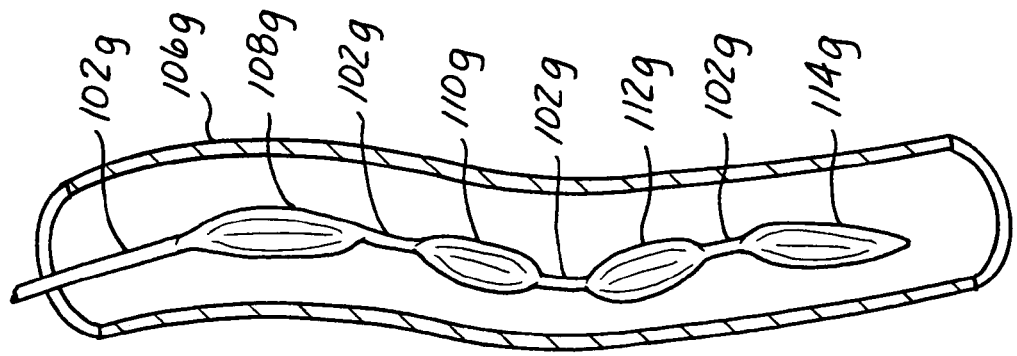
FIG. 4A is a detailed cross-section of a vascular entry into the aorta illustrating a quadruple chamber, large volume, long term intra-aortic balloon pump according to the present invention in a deflated state after insertion through an upper body skin entry point and/or upper body vascular entry point.

The long term intra-aortic balloon pump according to the present invention is intended for long term use. The phrase "long term" as used in conjunction with the LTIABP of the present invention refers to the ability of the LTIABP to be used by ambulatory patients for extended or prolonged periods of time, on the order of several months up to several years, compared with the relatively limited period of time, on the order of hours up to several days or weeks, capable of being used by sedentary patients on a single conventional temporary IABP. The long term intra-aortic balloon pump according to the present invention has increased inflated volume on the order of 50 cc to 654 cc, inclusive, which is comparable to the CARDIOVAD® permanent blood pump, rather than the 35 cc to 40 cc inflated volume provided by the conventional temporary IABP. To provide the desired inflated volume, the LTIABP according to the present invention is elongated along the longitudinal axis. The pumping chamber 108a, 108b of the LTIABP has tapered outer ends as illustrated in FIGS. 1A-1C and/or is segmented into one or more subsegments 108c-108h, 110c-110h, 112e-112h, 114g-114h, each subsegment separated by a flexible power conduit length 102c-102h as illustrated in FIGS. 2A-2C, 3A-3C, and 4A-4C. According to the present invention, the LTIABP is an intra-luminal balloon, and there is no increase in aorta cross section, as is the case with the CARDIOVAD® permanent blood pump. Since the LTIABP according to the present invention is longer, the pump chamber can straddle the diaphragm of the patient. In the segmented pumping chamber configuration according to the present invention, the chambers can have independent diameters with respect to one another, where the diameters decrease in diameter further along the aorta from the heart. This implies a configuration capable of being inserted from below the diaphragm upwardly within the aorta, and alternatively, another configuration capable of being inserted from an upper body point of entry downwardly within the aorta as illustrated in FIGS. 1A-1B, 2A-2B, 3A-3B, and 4A-4B. It should also be recognized that the present invention can be scaled down in size for special clinical circumstances, for example to accommodate a petite patient.

The LTIABP according to the present invention can be used with any skin access connector. By way of example and not limitation, the LTIABP according to the present invention can be used in combination with the percutaneous access device of the present invention as disclosed in U.S. Pat. No. 5,833,655, the specification of which is incorporated by reference herein. The PAD can be sized and shaped for surgical implantation in any desired location of the patient's body suitable for the particular skin entry point of the LTIABP. Furthermore, the PAD according to the present invention can be used with any balloon pump. By way of example and not limitation, the PAD according to the present invention can be used with a conventional temporary IABP to allow small vessel surgical entry while providing long term connection through the skin.

Suitable techniques for implantation of PAD 10 are known to the skilled artisan and include but are not limited to the method described in U.S. Pat. No. 4,634,422, the specification of which is incorporated by reference herein. The general type of PAD can be employed, for example, to supply a pneumatic connection and electrocardiogram lead connections to a dynamic aortic patch of the type disclosed in Kantrowitz et al, U.S. Pat. No. 4,051,840, the specification of which is incorporated by reference therein.

Figure 5:
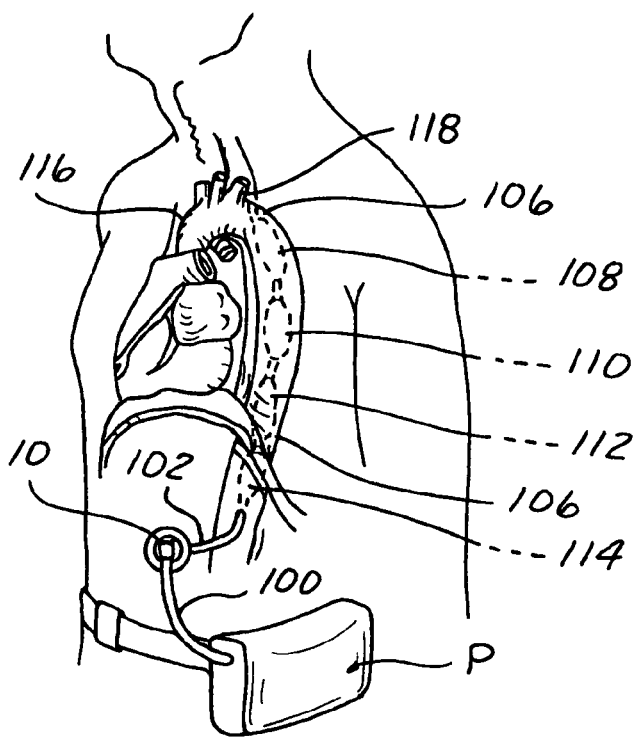
FIG. 5 is a schematic diagram illustrating the PAD device used in combination with an internally implanted balloon pump and an external monitoring/control pump device.
Figure 6:
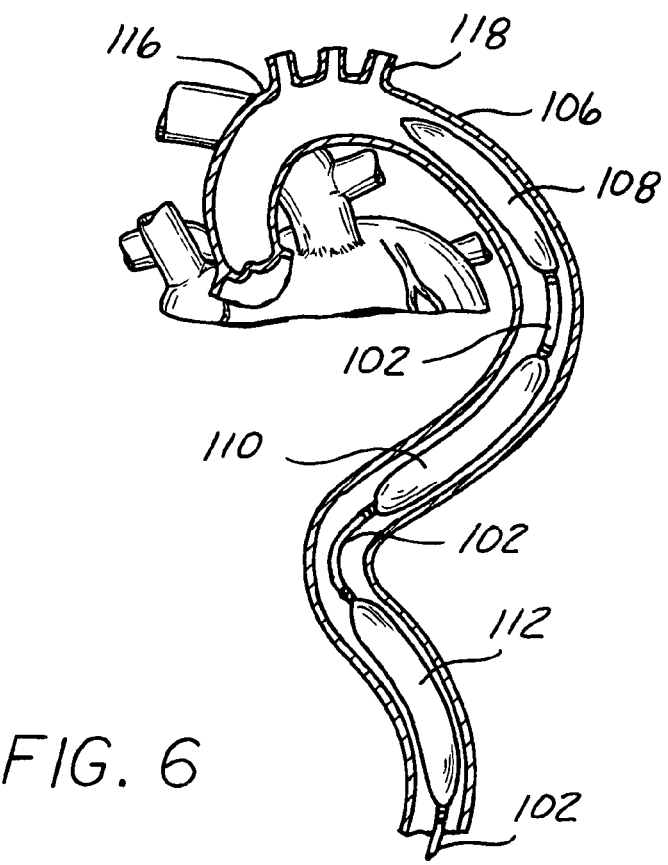
FIG. 6 is a partial view of a human heart and associated arteries showing in cross-section the position of a balloon pump according to the present invention within the descending aorta while depicting a three-dimensional serpentine tortuous descending aorta which has been exaggerated for purposes of illustration in the two-dimensional drawing.

Referring now to FIGS. 5 and 6, a catheter 102 attachable to a pump P is inserted into a descending aorta 106 within the body of a patient. The catheter is of relatively large diameter and is attached to a series of balloons 108, 110, 112, 114 which are pushed from an artery into the descending aorta 106 with the uppermost balloon 108 positioned in the descending aorta 106 below the aortic arch 116 and more particularly, downstream of the arch arteries 118. A plurality of balloons 108, 110, 112, 114 are spaced longitudinally from one another along the catheter 102 providing a total inflatable volume between 50 cc to 65 cc, and more particularly between 55 cc to 65 cc, and most particularly between 60 cc to 65 cc inclusive.

The external pump system P can supply a pressurized fluid, such as compressed air, while being operated according to a control program stored in memory in order to provide cardiac assistance to a patient. Additional details regarding suitable control programs and methods of operation adaptable for use with the present invention can be obtained from U.S. Pat. No. 5,833,619, U.S. Pat. No. 5,904,666, U.S. Pat. No. 6,042,532, U.S. Pat. No. 6,132,363 and U.S. Pat. No. 6,511,412, all of which are incorporated by reference herein in their entireties.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A long-term ambulatory intra-aortic balloon pump system for providing left ventricular cardiac assistance to a patient comprising:
   an external drive system for supplying a compressed fluid, the drive system operating in accordance with a control program stored in memory; and
   an intra-luminal balloon pump having at least two elongate inflatable chambers, the intra-luminal balloon pump positionable to be lying completely within a descending aorta of the patient, the at least two elongate inflatable chambers connectible in fluid communication for simultaneously inflating and deflating the at least two elongate chambers synchronously with a heartbeat of the patient in accordance with the control program stored in memory of the external drive system,
   wherein the at least two elongate inflatable chambers are configured in series along a conduit with adjacent elongate inflatable chambers longitudinally interposed with a flexible conduit link, the configuration allowing individual chambers to align relationship with along a local longitudinal axis of a corresponding local segment of surrounding aortic lumen in a non-planar, non-uniform radius of curvature relationship, and
   wherein the elongate inflatable chambers are individually sized such that an inflated chamber does not increase a cross-section of the local segment of surrounding aorta.

2. The system of claim 1 further comprising:
   a percutaneous access device implantable with respect to a patient for connecting in fluid communication with the compressed fluid to be supplied by the external drive system.

3. The system of claim 2, wherein the external drive system supplies compressed air to the percutaneous access device through a large diameter conduit.

4. The system of claim 1, wherein the at least two elongate inflatable chambers further comprises at least three elongate inflatable chambers longitudinally separated from one another in series by flexible conduit links allowing individual chambers to align along the local longitudinal axis of the corresponding a local segment of surrounding aortic lumen.

5. The system of claim 1, wherein the at least two elongate inflatable chambers further comprises at least four elongate inflatable chambers longitudinally separated from one another in series by flexible conduit links allowing individual chambers to align along the local longitudinal axis of the corresponding local segment of surrounding aortic lumen.

6. The system of claim 1 further comprising:
   each of the at least two elongate inflatable chambers having an inwardly tapering sidewall adjacent at least one end.

7. The system of claim 1 further comprising:
   each of the at least two elongate inflatable chambers having an inwardly tapering sidewall adjacent each longitudinal end.

8. The system of claim 1, wherein the at least two inflatable chambers has an inflated volume of between 50 cc to 65 cc, inclusive.

9. The system of claim 1, wherein the at least two inflatable chambers has an inflated volume of between 50 cc to 65 cc, inclusive.

10. The system of claim 1, wherein the at least two inflatable chambers further comprises a plurality of inflatable chambers increasing in size from a proximal location with respect to an end of an interconnecting conduit to a distal location with respect to the end of the interconnecting conduit for positioning in the descending aorta of the patient from a proximal insertion point with respect to the descending aorta.

11. The system of claim 1, wherein the at least two inflatable chambers further comprises a plurality of inflatable chambers decreasing in size from a proximal location with respect to an end of an interconnecting conduit to a distal location with respect to the end of the interconnecting conduit for positioning in the descending aorta of the patient from a distal insertion point with respect to the descending aortic tree and major branches.

12. The system of claim 1, wherein all of the at least two inflatable chambers of the elongate intra-luminal balloon pump are positionable to be lying located completely downstream of the aortic arch and it's major branches to the arm, head, and neck.

13. In a long-term ambulatory intra-aortic balloon pump system for providing left ventricular cardiac assistance to a patient, the improvement comprising:
   an intra-luminal balloon pump having a plurality of elongate inflatable chambers, the intra-luminal balloon pump positionable to be lying completely within a descending aorta of the patient and interconnected by a common fluid supply line for simultaneously inflating and deflating the plurality of elongate chambers synchronously with respect to a heartbeat of the patient,
   wherein adjacent elongate chambers are interposed with a flexible conduit link and separately and individually alignable with discrete local segments of surrounding aortic lumen in a non-linear relationship with respect to one another, and
   wherein the plurality of elongate inflatable chambers are individually sized such that an inflated chamber does not increase a cross-section of the associated segment of surrounding aorta lumen.

14. The system of claim 13, wherein the plurality of elongate chambers define a non-uniform radius of curvature with respect to one another.

15. The system of claim 13, wherein the plurality of inflatable chambers vary in size from a proximal location with respect to an end of an interconnecting conduit to a distal location with respect to the end of the interconnecting conduit for positioning in the descending aorta of the patient from one of a proximal insertion point with respect to the descending aorta, and a distal insertion point with respect to the descending aortic tree and major branches.

16. The system of claim 13 further comprising:
   a large diameter fluid power conduit connected with the plurality of inflatable chambers for communicating fluid to inflate and deflate the plurality of chambers simultaneously.

17. The system of claim 13, wherein the plurality of inflatable chambers have a total inflated volume of between 60 cc to 65 cc, inclusive.

18. A long-term ambulatory intra-aortic balloon pump system for providing left ventricular cardiac assistance to a patient comprising:
   an external drive system for supplying a compressed fluid, the drive system operating in accordance with a control program stored in memory;
   a percutaneous access device implantable with respect to a patient for connecting in fluid communication with the compressed fluid to be supplied by the external drive system, the percutaneous access device having an enlarged implantable flange portion with a reduced dimension neck portion extending outwardly to a location external of the patient for supporting a fitting for releasably connecting the compressed fluid supplied by the external drive system; and an intra-luminal balloon pump having at least two elongate inflatable chambers, the intra-luminal balloon pump positionable to be lying completely within a descending aorta of the patient, the at least two elongate inflatable chambers connectible in fluid communication with the percutaneous access device for simultaneously inflating and deflating each chamber synchronously with a heartbeat of the patient in accordance with the control program stored in memory of the external drive system, wherein the at least two elongate inflatable chambers are configured in series along a conduit with adjacent chambers longitudinally interposed with a flexible conduit link, the configuration allowing individual chambers to align along a local longitudinal axis of a corresponding local segment of surrounding aortic lumen in a non-planar, non-uniform radius of curvature relationship with respect to one another, and wherein the elongate inflatable chambers are individually sized such that an inflated chamber does not increase a cross-section of the associated segment of surrounding aorta lumen.

19. The system of claim 18 further comprising:
each of the plurality of elongate inflatable chambers having an inwardly tapering sidewall adjacent at least one end.

20. The system of claim 18 further comprising:
each of the plurality of elongate inflatable chambers having an inwardly tapering sidewall adjacent each longitudinal end.

21. The system of claim 18, wherein the external drive system supplies compressed air to the percutaneous access device through a large diameter conduit.

22. The system of claim 18, wherein the plurality of inflatable chambers increase in size from a proximal location with respect to an end of an interconnecting conduit to a distal location with respect to the end of the interconnecting conduit for positioning in the descending aorta of the patient from a proximal insertion point with respect to the descending aorta.

23. The system of claim 18, wherein the plurality of inflatable chambers decrease in size from a proximal location with respect to an end of an interconnecting conduit to a distal location with respect to the end of the interconnecting conduit for positioning in the descending aorta of the patient from a distal insertion point with respect to the descending aortic tree and major branches.

24. The system of claim 18, wherein all of the plurality of inflatable chambers of the elongate intra-luminal balloon pump are positionable to be lying located completely downstream of the aortic arch and carotid arteries.

* * * * *